US008262566B2

(12) United States Patent
Gilad et al.

(10) Patent No.: US 8,262,566 B2
(45) Date of Patent: Sep. 11, 2012

(54) DEVICE AND METHOD FOR UNIFORM IN VIVO ILLUMINATION

(75) Inventors: Zvika Gilad, Haifa (IL); Amit Pascal, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1058 days.

(21) Appl. No.: 12/172,422

(22) Filed: Jul. 14, 2008

(65) Prior Publication Data

US 2010/0010312 A1  Jan. 14, 2010

(51) Int. Cl.
*A61B 1/06* (2006.01)
*H04N 5/225* (2006.01)
(52) U.S. Cl. .............. 600/176; 600/160; 348/340
(58) Field of Classification Search .............. 600/109, 600/160, 176, 182
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,718,663 A * | 2/1998 | Wulfsberg | 600/176 |
| 5,993,378 A | 11/1999 | Lemelson | |
| 6,240,312 B1 | 5/2001 | Alfano et al. | |
| 7,009,634 B2 | 3/2006 | Iddan et al. | |
| 7,662,094 B2 * | 2/2010 | Iddan | 600/176 |
| 7,821,564 B2 * | 10/2010 | Avron et al. | 348/340 |
| 2001/0051766 A1 * | 12/2001 | Gazdzinski | 600/309 |
| 2002/0103417 A1 | 8/2002 | Gazdzinski | |
| 2004/0171914 A1 | 9/2004 | Avni | |
| 2005/0020880 A1 | 1/2005 | Miyake et al. | |
| 2005/0049462 A1 * | 3/2005 | Kanazawa | 600/170 |
| 2005/0179805 A1 * | 8/2005 | Avron et al. | 348/340 |
| 2006/0004256 A1 * | 1/2006 | Gilad et al. | 600/160 |
| 2006/0004257 A1 | 1/2006 | Gilad et al. | |
| 2007/0002135 A1 * | 1/2007 | Glukhovsky | 348/77 |
| 2007/0191683 A1 * | 8/2007 | Fujimori | 600/173 |
| 2009/0059003 A1 * | 3/2009 | Kim | 348/143 |
| 2011/0028786 A1 * | 2/2011 | Orihara | 600/109 |

FOREIGN PATENT DOCUMENTS

| | | |
|---|---|---|
| DE | 344 0177 | 5/1986 |
| EP | 1 371 321 | 12/2003 |
| EP | 1 741 382 | 1/2007 |
| EP | 2 031 863 | 3/2009 |
| JP | 57-45833 | 3/1982 |
| JP | 4-109927 | 4/1992 |
| JP | 1992-144533 | 5/1992 |
| WO | WO 2004/028336 | 4/2004 |
| WO | WO 2008/027448 | 3/2008 |

OTHER PUBLICATIONS

Search Report of EP Application No. 09 16 5457 mailed on Oct. 21, 2009.
Office Action of EP Patent Application No. 09 165 457.4 mailed on Aug. 27, 2010.

* cited by examiner

*Primary Examiner* — Philip R Smith
*Assistant Examiner* — William Chou
(74) *Attorney, Agent, or Firm* — Pearl Cohen Zedek Latzer, LLP

(57) ABSTRACT

An in vivo imaging device comprises a viewing window, an illumination unit, a lens holder and a light guide. The light guide may be positioned to create uniformly dispersed illumination and to eliminate backscatter from the viewing window. The light guide may guide light from the illumination unit to a desired position within the in vivo device. In one embodiment, the light guide may be embedded into the lens holder.

12 Claims, 9 Drawing Sheets

DEVICE AND METHOD FOR UNIFORM IN VIVO ILLUMINATION

FIELD OF THE INVENTION

The present invention relates to a device useful for in-vivo imaging, more specifically to a device for providing uniform illumination in-vivo.

BACKGROUND OF THE INVENTION

Known devices may be helpful in providing in-vivo imaging. Autonomous in-vivo imaging devices, such as swallowable capsules or other devices may move through a body lumen, imaging as they move along. In an in-vivo imaging device having a certain field of view (FOV) and incorporating a corresponding illumination system, the illumination is achieved by one or more light sources having a certain field of illumination (FOI).

Reference is now made to FIG. 1A, showing a schematic two dimensional presentation of an optical system according to an embodiment of the prior art. Referring to FIG. 1A, optical system generally referenced 100 may be included in, an in-vivo imaging device, but may be included in other suitable devices, such as an endoscope, trocar, or other in-vivo imaging device. Optical system 100 may include, for example, light sources 142 and 143, an imager 146, and one or more optical heads 149 (which may comprise lenses and a lens holder or a lens cover) disposed behind a viewing window such as optical dome 154, for viewing, for example, a target or object 115. One, two, or more than two illumination sources may be used. FOI 142' (indicated by dots) defines the area illuminated by light source 142, while FOI 143' (indicated by asterisks) defines the area illuminated by light source 143.

The FOI illuminated by each light source, such as light sources 142 and 143, is typically stretched over a relatively wide area, with a varying intensity of illumination that is proportional to the distance from the light source. A ray of light, for example ray 150, may exit a light source, for example light source 142, and reflect back from the dome 154 through the optical head 149 to the imager 146. Such reflected rays, which are typically viewed as bright white spots in the image, may cause a partial obstruction of the image.

FIG. 1B is an exemplary graphical illustration of the illumination distribution within a FOI, such as FOI 142' or 143', of a single light source, for example a commercially available white LED. The illumination distribution within a FOI of a light source is best described as a Gaussian distribution as characterized by the Gaussian curve 180. In cases where four light sources are employed, for example within an optical system of an in-vivo imaging device, four overlapping areas are created between the FOI of each light source. For example, as depicted in FIG. 1C, for each light source 142, 143, 144 and 145 four FOI 142', 143', 144' and 145' exist, respectively. The partial overlaps between FOI of each light source may create four distinct areas which are strongly illuminated whereas in other areas illumination may be diminished in comparison. For example, as depicted in FIG. 1D, the area created at the conjunction of the four overlapping FOI 142', 143', 144' and 145' is strongly illuminated, while other areas are more weakly illuminated.

A frequent problem encountered in optical systems for in vivo imaging is that stray light and backscatter may reflect from the optical window of the in vivo device. Such stray light may be received by the receiving means (e.g., an image pickup element) and cause partial obstruction of the image due to the reflections, which are typically viewed as bright white spots in the image.

There is a need for an in vivo device that will provide unvarying, uniform illumination in the in-vivo device field of view, with minimal impediment of stray light reflections.

SUMMARY OF THE INVENTION

The present invention introduces a device and method for providing a uniform field of illumination for an in vivo imaging device.

An embodiment of the device of the present invention may comprise a viewing window, an illumination unit, a lens holder and a light guide. The light guide may be positioned to create uniformly dispersed illumination and to eliminate backscatter from the viewing window. The light guide may guide light from the illumination unit to a desired position within the in vivo device. In one embodiment, the light guide may be embedded into the lens holder. The lens holder may provide additional functionality, such as securely supporting the optical elements of the imaging device, centering them along an optical axis, and fixing their position and/or distance relative to the viewing window or the housing of the device.

In one embodiment, the viewing window may be structured as an ellipsoid, and the light guide may be positioned on a focal curve of the ellipsoid to eliminate reflections of stray light from the viewing window. The device may comprise a housing, wherein the illumination unit may be contained within the housing and behind the viewing window.

In one embodiment, the light guide may comprise optical fibers or transparent plastic material. According to one embodiment, the in-vivo imaging device may be a swallowable capsule.

According to one embodiment, there is provided a method for the manufacture of an in vivo imaging capsule, the method comprising the steps of: installing a substrate and a light source behind a viewing window; installing on the substrate a lens holder comprising a light guide, said light guide to direct illumination from said light source to a focal curve of the viewing window; and encapsulating the substrate in a housing of the in vivo imaging capsule. According to one embodiment, the illumination directed to a focal curve of the viewing window may create a consistent field of illumination, for example while the device is in vivo.

According to one embodiment, there is provided a method of in vivo imaging, the method comprising guiding illumination from a light source within an imaging capsule to a position within the imaging capsule from which the light is substantially uniformly dispersed and backscatter is substantially eliminated.

BRIEF DESCRIPTION OF THE DRAWINGS

The present invention will be understood and appreciated more fully from the following detailed description taken in conjunction with the drawings in which.

Figure 1A:
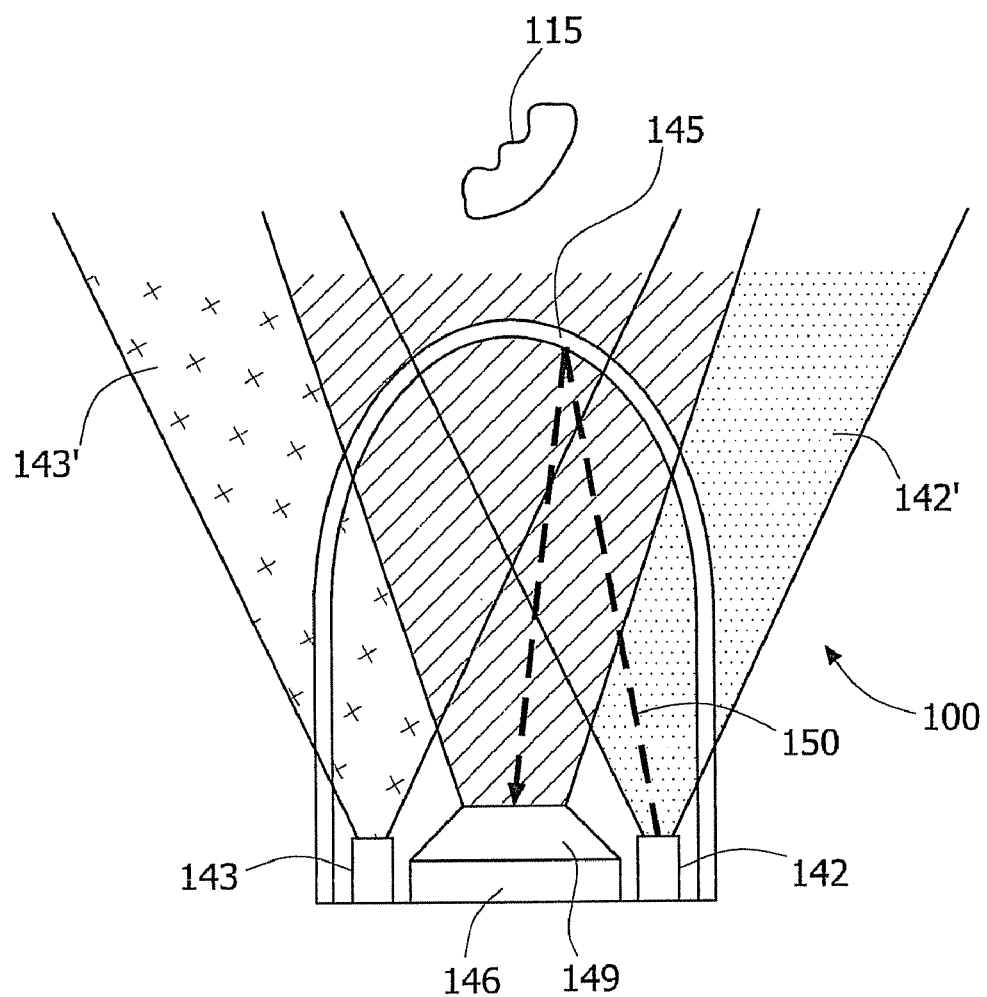
FIG. 1A, showing a schematic two dimensional presentation of an optical system according to an embodiment of the prior art.
Figure 1B:
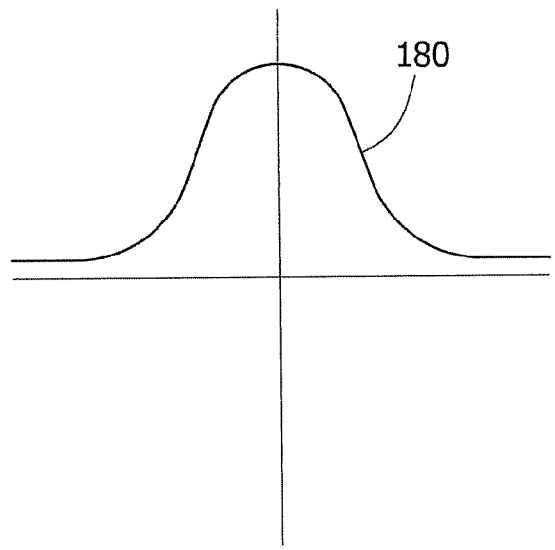
FIGS. 1B-1D are exemplary graphical illustrations of illumination distributions, according to the prior art.
Figure 1C:
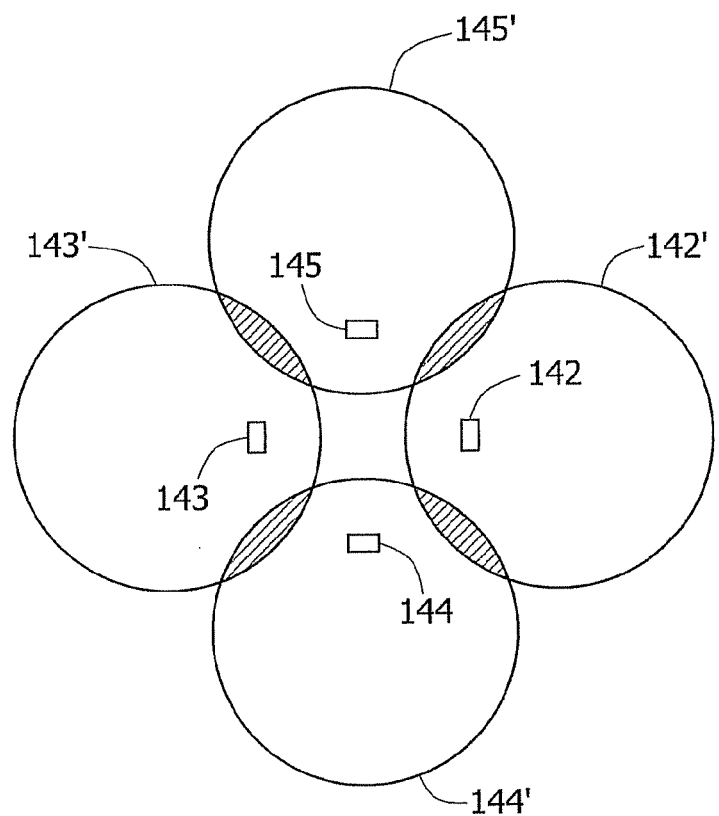

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Figure 2:
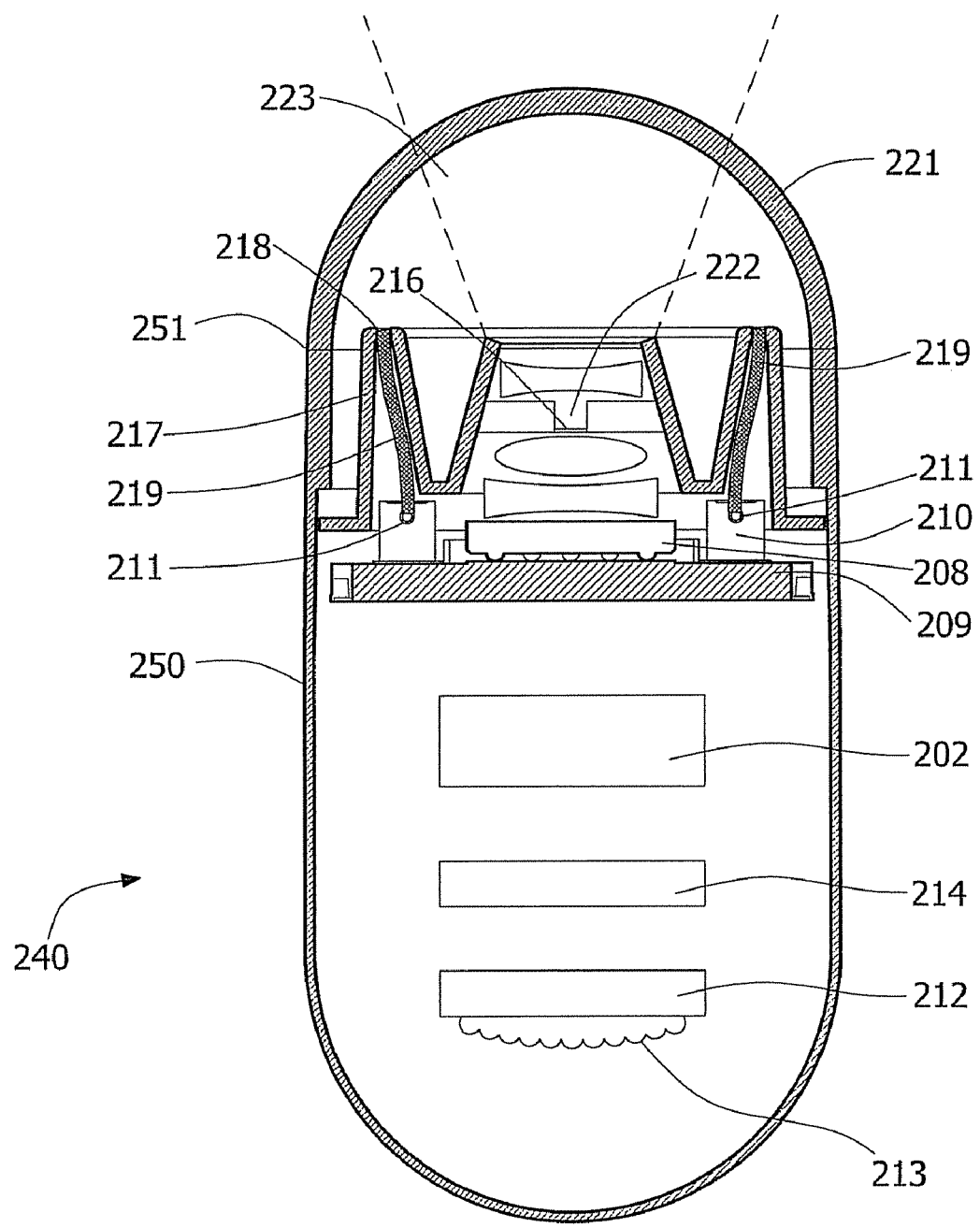
FIG. 2 schematically illustrates an in vivo imaging device according to an embodiment of the invention.

Reference is now made to FIG. 2, which schematically illustrates an in vivo imaging device according to an embodiment of the invention. According to one embodiment, the device 240 may include a housing 250 and a dome or viewing window 221. The housing 250 may contain or enclose an imaging system for obtaining images from inside a body lumen, such as the GI tract. The imaging system may include one or more illumination units 210, an image sensor for example an imager 208 and an optical unit 222 which focuses the images onto the imager 208.

Inaccuracy of the illumination unit's position in the imaging device may be caused by several factors, which will be explained in detail herein below:
tolerance of the assembly process of the illumination unit (e.g. LED) on the electrical circuit;
tolerance of the exact position of the die which produces the light inside the illumination unit; and/or
tolerance of the positioning of the dome or viewing window in relation to the optical unit, the optical axis and the illumination unit.

All the factors mentioned above may contribute to an accumulated error in the placement of the illumination unit, which may cause stray light reflections from the viewing window, and an inconsistent FOI. LEDs (Light Emitting Diode) which are typically used as illumination units, are intrinsically imprecise components which may vary, for example, in their illumination intensity, physical size, angle of the die in its LED package, and position of the die relative to its package. LEDs do not approximate a "point source" of light (for example a pin-point source), and therefore are difficult to use in applications needing a highly collimated beam. Such illumination typically causes stray light to hit the dome of the imaging device, and reflect back to the imager, possibly causing bright white spots and partial obstruction of the image.

The illumination unit 210 may illuminate the inner portions of the body lumen through viewing window or dome 221. The illumination unit 210 typically has a certain width, length, and surface area, which may prevent the possibility of positioning it accurately on a certain point on the support or substrate 209, for example on the focal curve of the dome 221. In addition, the illumination unit may comprise a light source, for example a LED, which typically has a size tolerance that may change the actual size and intensity of the illuminated area (or FOI) created by it.

Furthermore, the FOI may be affected by the spatial tolerance of an illumination unit which is positioned in a device, which may be created for example due to a variance in the angle that the illumination unit is connected to the support or substrate. Additional variance may be created, for example during the device assembly process, in the exact location of the illumination unit in relation to the optical unit components or axis, and/or the dome of the device.

In order to solve these variance and tolerance problems, the lens holder 217 may be designed such that it securely holds the optical components (e.g., lenses, iris and imager) which are contained in it, thereby enabling accurate positioning of the optical components in relation to the optical axis. According to a preferred embodiment, the lens holder 217 may also comprise a light guide means 219, thereby eliminating the tolerance of the illumination unit positioning and centering relative to the optical unit. In some embodiments, the light guide means may comprise a light pipe, which may typically be a made of a rigid material. The light pipe may be plated or coated on its internal side by a reflecting substance, such as silver, aluminum, or other multi-dialectical coating, or it may be designed as a total internal reflection light pipe. The shape of the light pipe may be conical, as shown in FIG. 3C, in order to reduce or minimize the size (or area) of the light source exit, and achieve a nearly spot-like or nearly linear source which will be located on the focal curve of the dome and thus reduce stray light reflected from the dome. In other embodiments, the light guide means may comprise optical fiber bundles, which are typically made of flexible material. The optical fiber may be single mode fiber bundles, which are typically narrower and with a smaller numerical aperture angle (NA). In other embodiments, the optical fibers may be multi-mode, typically adapted for larger illumination sources. The lens holder 217 may also be designed to touch the inner surface of the dome 221, in order to prevent movement or shifting of the optical elements and the illumination relatively to the dome 221 or the housing 250 of the device 240. Typically, the lens holder 217 is made of non-transparent material such as plastic or metal. The iris 216 may be positioned below one lens or below a plurality of lenses, in order to broaden the FOV of the device, for example to enable a viewing angle of 160-170 degrees.

Figure 1D:
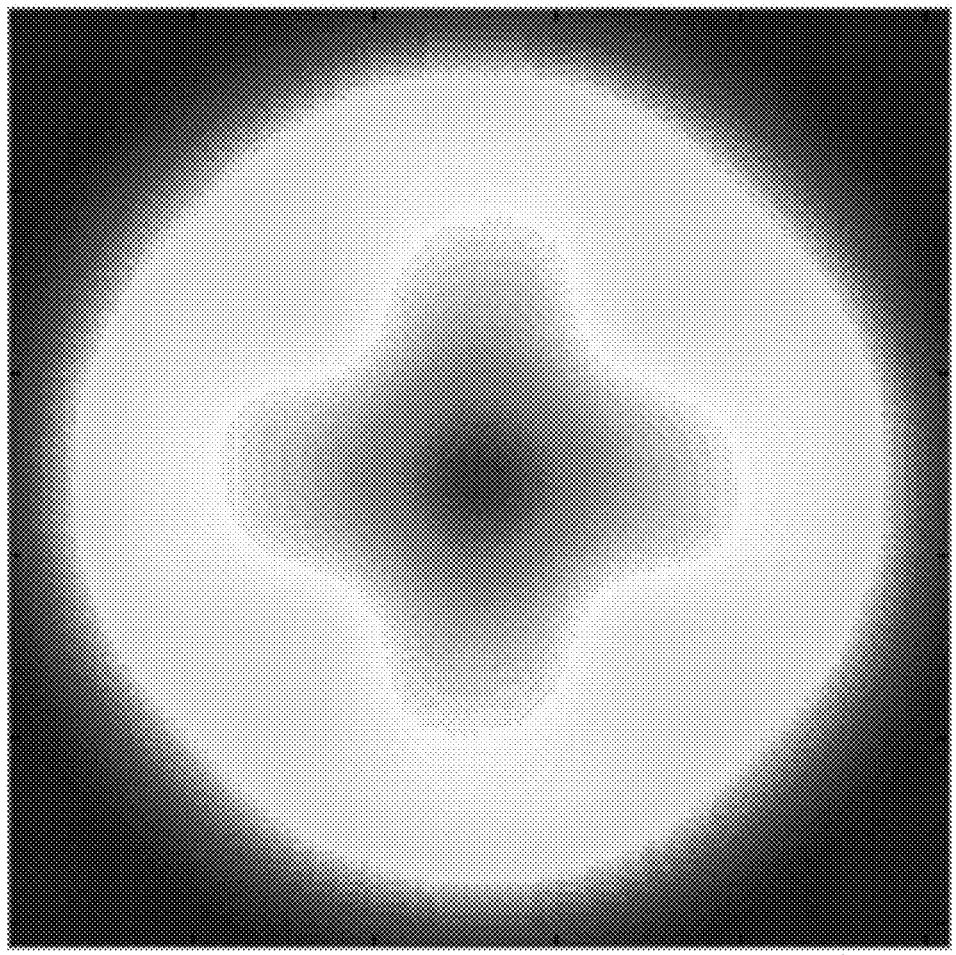

In prior solutions, the illumination map created by the illumination unit may be partially obscured by the optical unit or by the lens holder. For example as shown in FIG. 1D, the optical unit may cause a shadow which affects the FOI, thereby creating a varying, inconsistent illumination of the FOV. According to an embodiment of the present invention, the illumination unit 210 may be positioned at any location in the imaging device, such that it does not obscure the FOV. By deploying a light guide means 219 that directs the light from a source to a specific point or to a specific curve in the imaging device, the FOI that is created may be more uniform since reflections from the viewing window or dome of the imaging device may be substantially eliminated. In addition, according to one embodiment the light is directed to a plane located above the optical system (for example on the same plane or above the top end of lens holder 217), in order to prevent the shadow and/or obstruction of the FOI by the optical system. Furthermore, the size and number of illumination units does not affect the FOI, since the light is guided by very precise components to the specific point(s) required. For example, instead of deploying several illumination units, a single illumination unit which provides a strong illumination may be used.

In one embodiment, the illumination unit 210 may be placed adjacent the lens holder 217 (e.g. below it), or behind a support surface such as support 209, or even behind the power source(s) 202 of the imaging device. The light guide means 219 may comprise optical fibers, or transparent plastic light guide units, which may transfer the light from the illumination unit 210 to the light source exit 218. Thus, the illumination unit may be placed in the most convenient position for packaging of the optical head, without having to take into account FOI issues. According to some embodiments of the present invention the illumination unit 210 may include a light source 211, such as a white LED and/or an OLED.

The optical unit 222 may include, for example, a set of lenses which may be held by a lens holder 217. For example, 3, 4 or a different number of lenses may be included in the optical unit. In a preferred embodiment, the lower lens may be placed adjacent to the imager 208, and the other lenses may be placed one on top of the other to create an optical tower. The lens holder 217 may be positioned adjacent or leaning on the dome 221, in order to eliminate possible shifting or movement of the optical system in relation to the dome 221. In addition, the lens holder may be positioned adjacent or touching the optical components (the lenses, the iris 216 and the imager 208 for example) in order to eliminate or substantially reduce the tolerance caused by possible shifting or movement of the optical components in relation to the axis of the optical unit 222.

According to one embodiment, the lens holder may comprise one or more plastic tunnels, or optical fibers, or a combination of these, for example light guide 219, which may accurately direct the light from the illumination unit/s 210 to the light source exit point(s) 218. The light source exit 218 may be a pinpoint light exit, and may preferably be positioned on the focal curve of dome 221. For example, if dome 221 is configured as an ellipsoid (or ellipsoid-like), the light source exit 218 may be positioned accurately on a plurality of points on the focal curve of the ellipsoid or ellipsoid-like dome. Such a configuration may prevent backscatter and reflections from the dome back to the iris 216, while it may retain uniform light dispersion. The ellipsoid may become an ellipsoid-like structure, primarily due to the actual width of the lens holder which is placed on the focal curve; ideally this width would be close to zero, however this may not be mechanically practical since the lens holder has a certain width. According to one embodiment, it is possible to shorten the length of the dome 221, such that it reaches only the edge 251 of the lens holder (and not necessarily continues below to the level of the illumination units). The housing 250 of the device may therefore become longer, while the length of the dome may become shorter. A lengthy dome is more difficult to manufacture than a short dome, since the width should typically be very accurate, and the transparency should typically be very good with no scratches that may impair the FOV. The housing is more easily manufactured since it is not transparent. Therefore this embodiment may have the advantage of an easier manufacturing process of the dome and the device itself.

Device 240 may further include a control unit 214, a transmitter 212, a power source 202, such as a silver oxide battery, that provides power to the electrical elements of the device 240, and an antenna 213 for transmitting and/or receiving signals. For example, the antenna 213 may be used to transmit image signals from the imager 208. A suitable imager 208 may be, for example, a "camera on a chip" type CMOS imager. Other suitable types of imagers may be used, for example, a CCD imager. The single chip camera can provide signals for either black and white or color images. A suitable transmitter may comprise a modulator which receives the image signal (either digital or analog) from the CMOS imaging camera, a Radio Frequency (RF) amplifier, an impedance matcher and an antenna. A processor, e.g., for processing the image data may be included in the device. The processor or processing circuitry may be integrated in the sensor or in the transmitter.

According to some embodiments the device 240 may be capsule shaped and can operate as an autonomous endoscope for imaging the GI tract. However, other devices, such as devices designed to be incorporated in an endoscope, catheter, stent, needle, etc., may also be used, according to embodiments of the invention. Furthermore, the device 240 need not include all the elements described above. For example, the device 240 need not include an internal power source; power may be provided from an external source, for example, as known in the art.

According to one embodiment of the invention, various components of the device 240 may be disposed on a support 209 such as a circuit board including for example rigid and flexible portions; preferably the components are arranged in a stacked vertical fashion. In alternate embodiments, other arrangements of components may be placed on a circuit board having rigid portions connected by flexible portions. Such circuit boards may be similar to embodiments described in US Patent Publication number 2006/0004257 entitled IN VIVO DEVICE WITH FLEXIBLE CIRCUIT BOARD AND METHOD FOR ASSEMBLY THEREOF, and US Patent Publication number 2004/0171914 entitled IN VIVO SENSING DEVICE WITH A CIRCUIT BOARD HAVING RIGID SECTIONS AND FLEXIBLE SECTIONS, each incorporated by reference herein in their entirety. In alternate embodiments, a circuit board having rigid portions and flexible portions may be used to arrange and hold components in other in vivo sensing devices, such as a swallowable capsule measuring pH, temperature or pressure, or in a swallowable imaging capsule having components other than those described above.

Device 240 typically may be or may include an autonomous swallowable capsule, but device 240 may have other shapes and need not be swallowable or autonomous. Embodiments of device 240 are typically autonomous, and are typically self-contained. For example, device 240 may be a capsule or other unit where all the components are substantially contained within a container or shell, and where device 240 does not require any wires or cables to, for example, receive power from an external source or transmit information. Device 240 may communicate with an external receiving and display system to provide display of data, control, or other functions. Other embodiments may have other configurations and capabilities. For example, components may be distributed over multiple sites or units. Control information may be received from an external source.

Devices according to embodiments of the present invention, including imaging, receiving, processing, storage and/or display units suitable for use with embodiments of the present invention, may be similar to embodiments described in U.S. Pat. No. 7,009,634 entitled A DEVICE AND SYSTEM FOR IN VIVO IMAGING, which is assigned to the common assignee of the present invention and which is hereby incorporated by reference. Of course, devices and systems as described herein may have other configurations and other sets of components.

In one embodiment, all of the components may be sealed within the device body (the body or shell may include more than one piece); for example, a control unit 214, an imager 208, an illumination unit 210, power source 202, and transmitting 212 and control 214 units, may all be sealed within the device body.

Figure 3A:
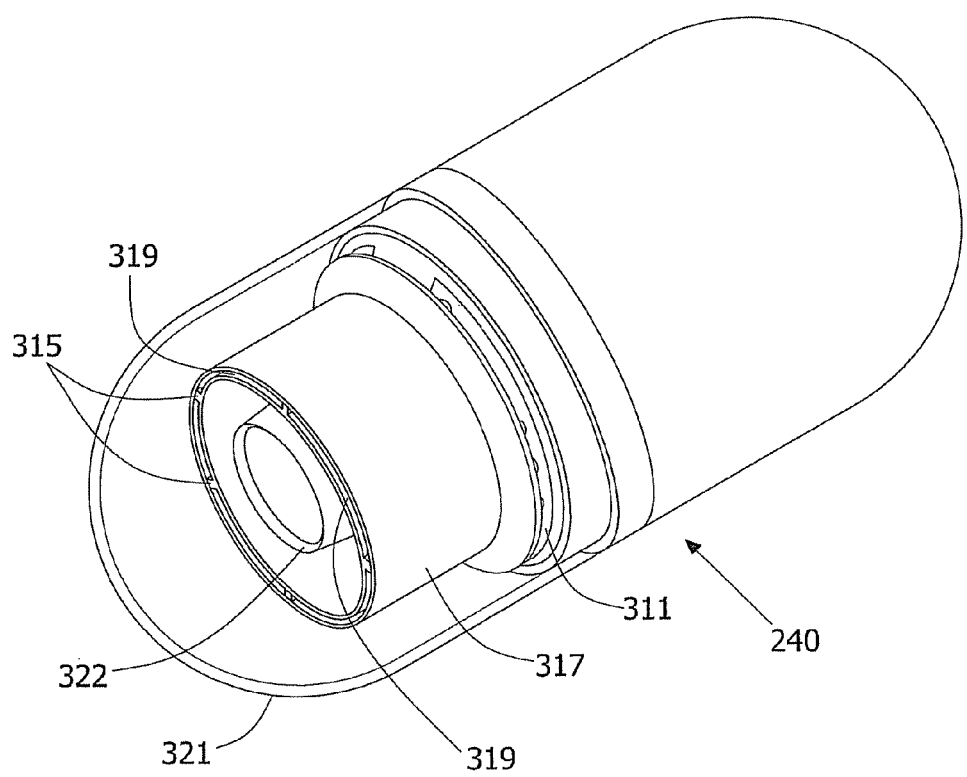
FIGS. 3A-3C schematically illustrate a light guide means in an in vivo imaging device according to an embodiment of the invention.
Figure 3B:
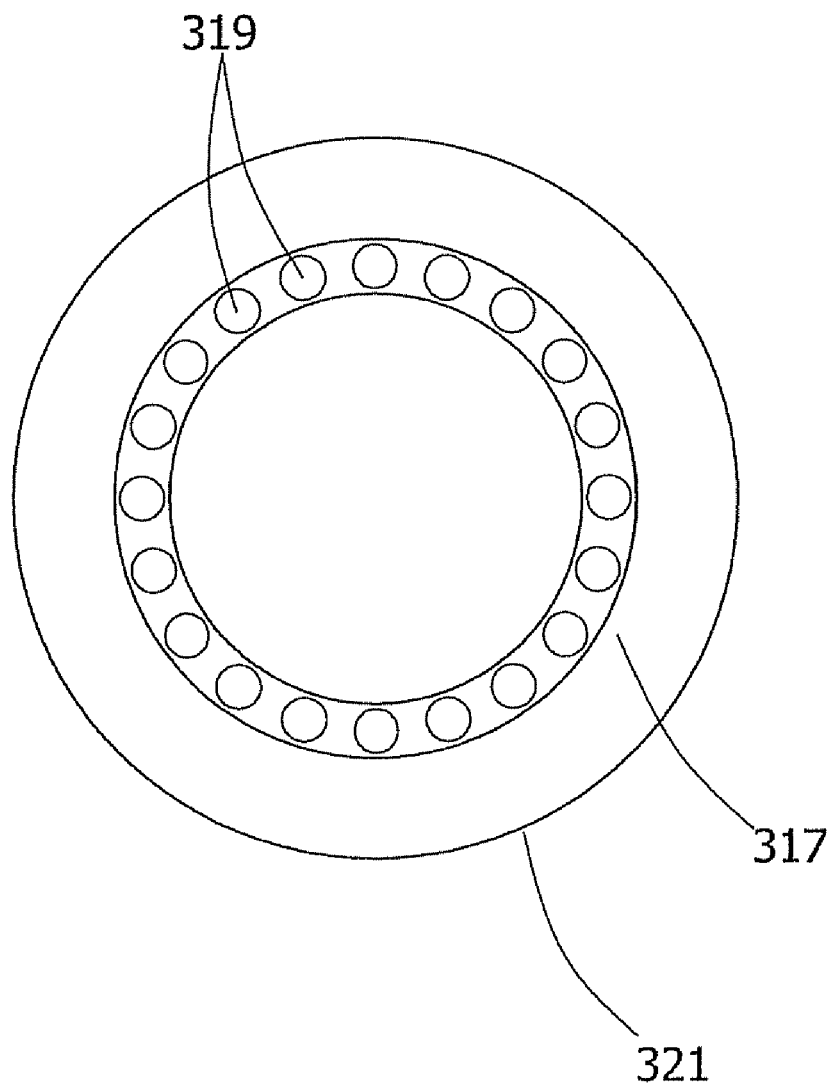
Figure 3C:
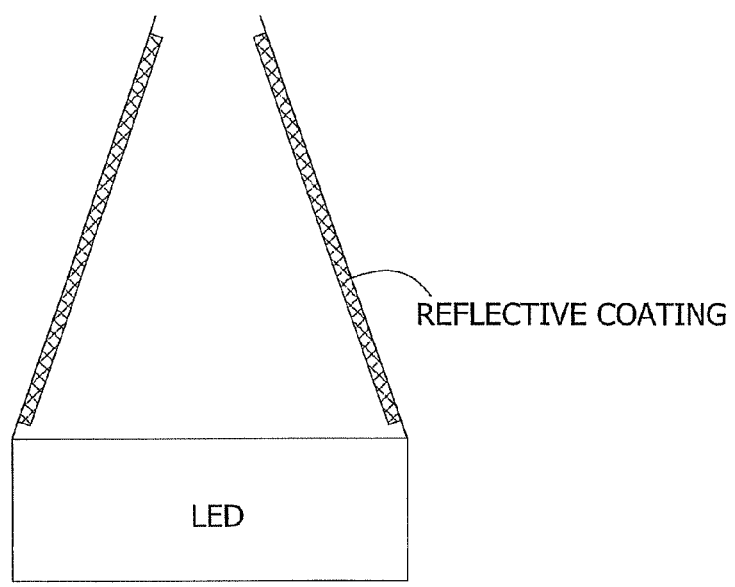

Reference is now made to FIGS. 3A and 3B, which schematically illustrate the light guide means in an in vivo imaging device according to an embodiment of the invention. In this figure, the light guide 319 is divided into tunnels embedded into the lens holder 317, and the light is directed to the focal curve of the ellipsoid dome. In this embodiment, the light is evenly distributed in, for example, five light guide 319 tunnels around the optical unit. Other number of tunnels is possible. The light guide 319 tunnels may be created due to the light guide manufacturing process, which may include the light guide as part of the lens holder, and connect to the lens holder surfaces in several points (such as contact points 315) in order to maintain the accurate positioning of the illumination on the focal curve and in relation to the optical unit and the dome which is required for improving the FOI.

In FIG. 3B a top view of the in vivo imaging device is shown, from the top of the dome 321 to the lens holder 317. In this embodiment, the light guide means is implemented using a large number of optical fibers 319, for example 20 bundles of optical fibers, that transfer the light from the illumination unit (not shown) to the focal curve of the dome 321. A different number of optical fibers may be used, for example 100 or 1000 fibers. A large number of fibers may be advantageous for increasing the uniformity of the FOI.

Figure 4:
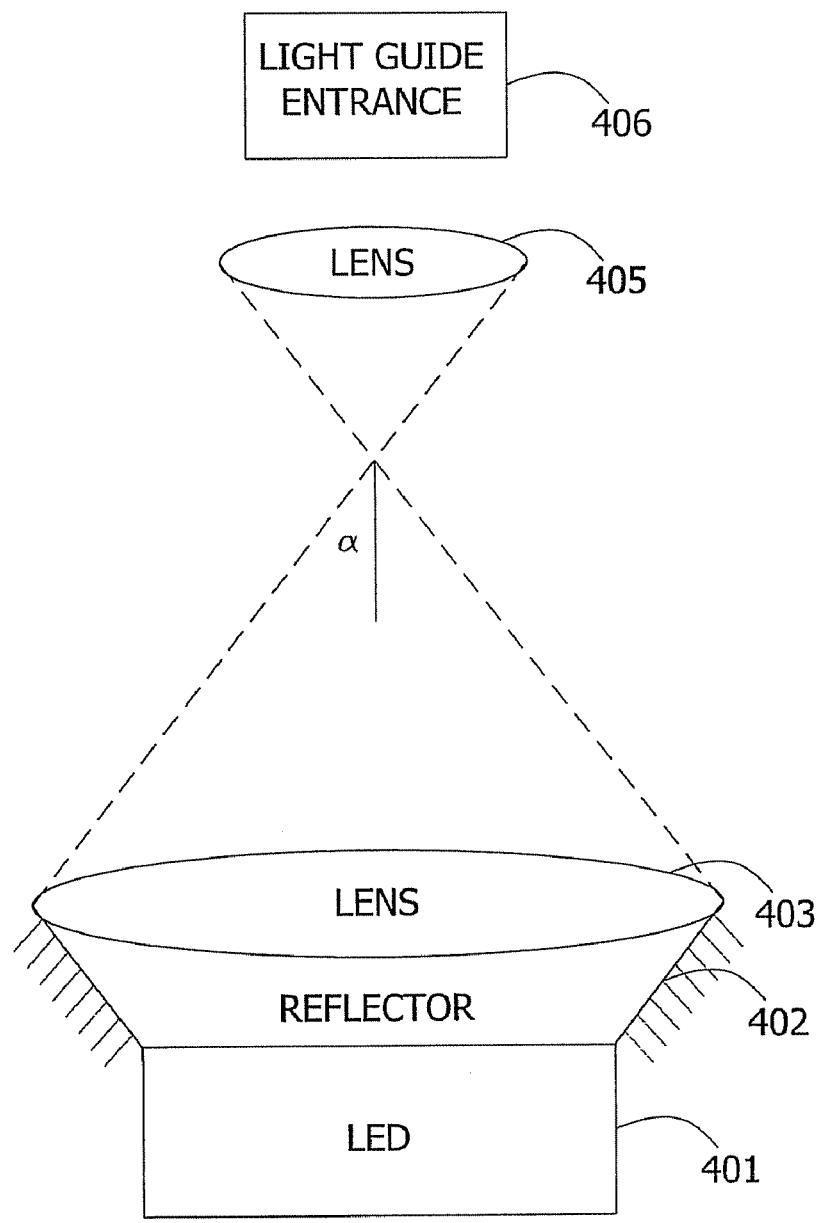
FIG. 4 illustrates a light source coupled with a light guide according to an embodiment of the invention.

Reference is now made to FIG. 4, which schematically illustrates an exemplary coupling means to couple a light source with a light guide according to an embodiment of the invention. Coupling the light source, for example an LED, to a light guide (for example an optical fiber bundle or a light pipe), may cause a substantial loss of the LED's illumination intensity. For example, in some cases, 50% or more of the illumination intensity may be lost in the passage of light from the LED to the light guide entrance 406. Different components may be used in order to solve this illumination loss. For example a reflector 402 may be coupled to the LED 401, in order to prevent (or partially prevent) light rays from the LED from diverging to different directions. Some light rays from the LED 401 which do not hit the reflector 402 may not enter the light guide entrance 406. In some embodiments, the light guide entrance 406 may only accept light which arrives in the range of a specific angle, which may be for example in case of optical fiber bundles the Numerical Aperture (NA) angle of the optical fiber. According to some embodiments, a condensing lens 403 may be used, for example in addition to the reflector 402 or instead of it, to collect the light rays coming from the LED 401 which may otherwise scatter to unwanted directions and not be directed to the light guide entrance 406. In some embodiments the angle α is larger than the NA of the optical fiber, an additional condensing lens 405 may be used to direct light rays into the light guide entrance 406. It is noted that in some embodiments, one or more of the components mentioned in this embodiment (reflector and condensing lenses) may be used to transfer the light efficiently from the light source to the light guide entrance.

Typically, the following equation will be retained:

$$\frac{P_{in}}{A_{in} * \Omega_{in}} = \frac{P_{out}}{A_{out} * \Omega_{out}}$$

wherein:

$A_{in}$ denotes the surface area of the illumination source and may be measured in $mm^2$;

$\Omega_{in}$ denotes the solid angle that the illumination source illuminates (three-dimensional), and may be measured in sr (steradian);

$A_{out}$, which denotes the area of the light rays exiting the light guide, may be measured in $mm^2$;

$\Omega_{out}$ denotes the solid angle of the exiting light rays, may be measured in steradian;

$P_{in}$ denotes the optical power that the light source emits (may be measured in Watt); and $P_{out}$ denotes the optical power that is emitted by the light pipe (may be measured in Watt).

Figure 5:
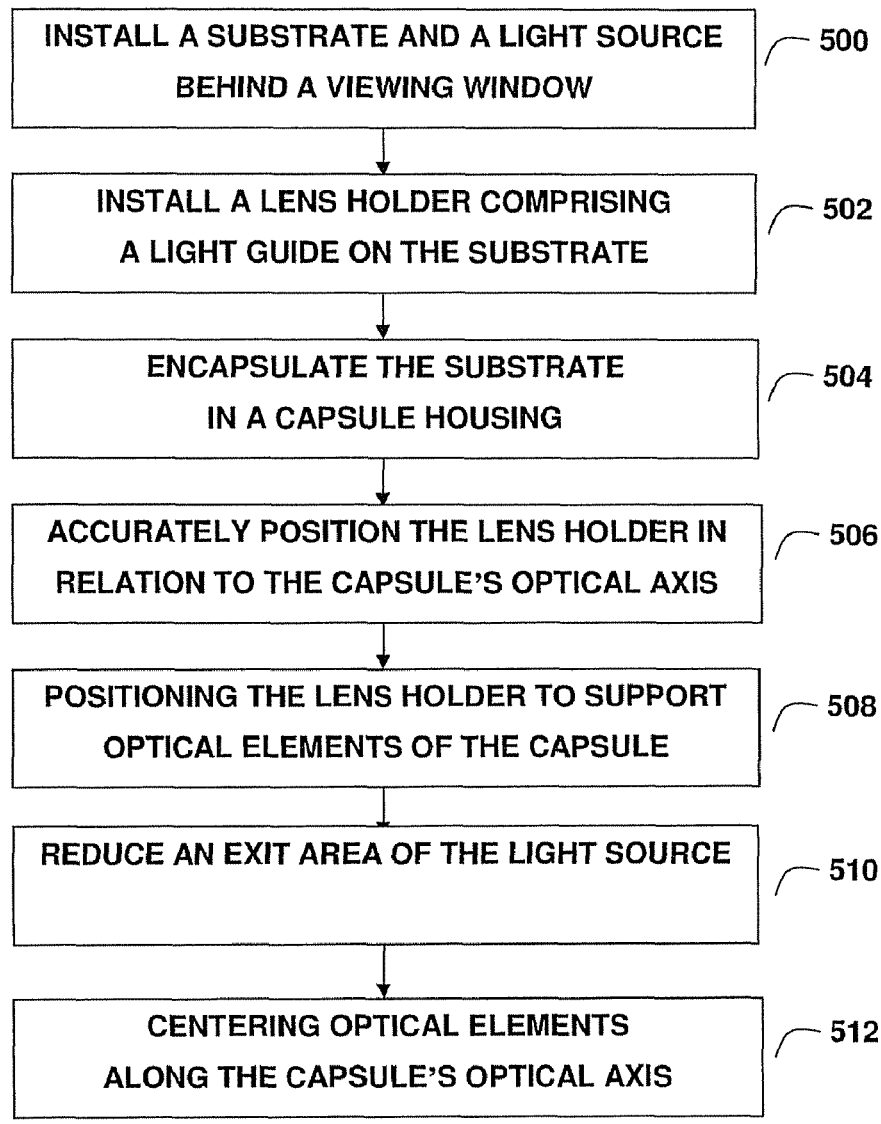
FIG. 5 is a flow chart illustrating a method of manufacture of an in vivo device according to an embodiment of the invention.

Reference is now made to FIG. 5, which is a flow chart illustrating a method of manufacture of an in vivo imaging capsule with a light guide according to an embodiment of the invention. In step 500, a substrate and a light source may be installed behind a viewing window of an in vivo imaging capsule. In step 502, a lens holder comprising a light guide may be installed onto the substrate. In step 504, the substrate may be encapsulated in a capsule housing, for example a plastic shell or a shell made from other waterproof material. In step 506, the lens holder may be accurately positioned in relation to the capsule's optical axis. In step 508, the lens holder may be positioned to support optical elements of the capsule, for example the lenses and/or the iris. For example, the lens holder may be adjacent the capsule housing, and may be touching it or leaning on it, or may be supported and held in place by it. The lens holder may be positioned such that it is touching the inner surface of the capsule's dome, in order to prevent movement or shifting of the optical elements and the illumination relatively to the dome or the housing of the capsule. In step 510, a light guide may be designed to reduce the area of the illumination exit of the light source, and to bring the illumination to the exact location of the plane of the focal curve of the capsule's dome, thereby reducing the occurrence of stray light from the dome. The illumination exit area may be reduced to a nearly linear curve, to achieve reduction of stray light. In step 512, optical elements such as the lenses, the imager and the iris, may be centered along the capsule's optical axis in order to achieve an accurate optical system with minimum reflections from the capsule's dome. It is noted that in some embodiments, all or some of the above mentioned steps may be performed.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A device for in vivo imaging comprising:
   a dome-shaped window;
   a substrate perpendicular to a device's optical axis;
   an illumination unit;
   a light guide;
   an image sensor installed on said substrate, said image sensor centered along the device's optical axis,
   wherein said illumination unit illuminates an object through said light guide and through said window and wherein said image sensor collects light reflected from the object through said window;
   a lens holder centered along the device's optical axis and having a first end that is adjacent to the apex of the window, said first end being closer to the apex of the window than the illumination unit and at least partially obscuring a field of illumination of said illumination unit; and
   wherein said light guide is to guide light from the illumination unit to a light source exit area at the same plane of the first end of the lens holder or at a plane closer to said apex of said window than said first end of the lens holder, said planes being parallel to the substrate plane.

2. The device according to claim 1 wherein the dome-shaped window is structured as an ellipsoid, and wherein said light is guided to a focal curve of the ellipsoid.

3. The device according to claim 1, wherein said light guide comprises optical fibers.

4. The device according to claim 1, wherein said light guide comprises a light pipe.

5. The device according to claim 4, wherein said light guide is shaped to reduce the light exit area of the illumination unit.

6. The device according to claim 1, wherein said illumination unit is a LED or an MED.

7. The device according to claim 6, wherein said light guide comprises a plurality of optical fibers for guiding light from said LED or OLED to the light source exit area, to provide uniformly dispersed illumination.

8. The device according to claim 1, wherein said in-vivo imaging device is a swallowable capsule.

9. The device according to claim 1, wherein said lens holder comprises a tunnel ending at said exit area and wherein said light guide is disposed within said tunnel.

10. The device according to claim 1, wherein said light guide comprises a plurality of optical fibers for guiding light from said illumination unit to said light source exit area.

11. A method for manufacture of an in vivo imaging capsule, the method comprising the steps of:
    installing on a substrate an imager and a light source behind a dome-shaped window, said substrate perpendicular to the imaging capsule's optical axis, and said light source;
    installing on the substrate a lens holder centered along the imaging capsule's optical axis and having a first end that is adjacent to the apex of the window, said first end being closer to the apex of the window than the light source and at least partially obscuring a field of illumination of said light source, and a light guide, said light guide to direct illumination from said light source to a light source exit area at the same plane of said first the end of the lens holder or at a plane closer to said apex of said window than said first end of the lens holder, said planes being parallel to the substrate; and
    encapsulating the substrate in a housing of the in vivo imaging capsule.

12. The method of claim 11 further comprising: reducing the exit area of the light source to achieve a nearly linear illumination exit.

* * * * *